(12) United States Patent
Bailly et al.

(10) Patent No.: US 11,098,422 B2
(45) Date of Patent: Aug. 24, 2021

(54) METHOD FOR FORMING A BARBED SUTURE AND THE BARBED SUTURE THUS OBTAINED

(71) Applicant: Sofradim Production, Trévoux (FR)

(72) Inventors: Pierre Bailly, Caluire-et-Cuire (FR); Alfredo Meneghin, Laval (FR); Sebastien Francois, Jassans-Riottier (FR); Xavier Couderc, Ain (FR)

(73) Assignee: Sofradim Production

( * ) Notice: Subject to any disclaimer, the term of this patent is extended or adjusted under 35 U.S.C. 154(b) by 245 days.

(21) Appl. No.: 16/208,728

(22) Filed: Dec. 4, 2018

(65) Prior Publication Data

US 2019/0105041 A1   Apr. 11, 2019

Related U.S. Application Data

(62) Division of application No. 15/095,518, filed on Apr. 11, 2016, now Pat. No. 10,178,991.

(30) Foreign Application Priority Data

Apr. 22, 2015  (EP) .................................... 15305604

(51) Int. Cl.
   *D04B 21/20* (2006.01)
   *A61B 17/06* (2006.01)
   *A61B 17/00* (2006.01)
(52) U.S. Cl.
   CPC ...... *D04B 21/202* (2013.01); *A61B 17/06166* (2013.01); *A61B 2017/00526* (2013.01); *A61B 2017/06176* (2013.01); *D10B 2509/04* (2013.01)

(58) Field of Classification Search
   CPC ........ D04B 21/202; A61B 2017/06166; A61B 2017/06176; A61B 2017/0619
   See application file for complete search history.

(56) References Cited

U.S. PATENT DOCUMENTS

| 71,909 A | 12/1867 | Pierce |
| 549,555 A | 11/1895 | White |

(Continued)

FOREIGN PATENT DOCUMENTS

| EP | 1075843 A1 | 2/2001 |
| EP | 2156795 A2 | 2/2010 |

(Continued)

OTHER PUBLICATIONS

European Search Report for EP 15305604.9 date of completion is Jul. 1, 2015 (5 pages).

*Primary Examiner* — Danny Worrell (57) ABSTRACT

The invention relates to a method for forming a barbed suture (10) comprising:
a) producing a knit by knitting together i) a set of chain stitch yarns (1) producing chain stitches and ii) a set of monofilament weft yarns completing weft stitches with at least one of said chain stitches, thereby producing at least one weft stitched chain stitch (6),
b) cutting the knit along the warp direction on both sides of said weft stitched chain stitch, so as to isolate said weft stitched chain stitch from the rest of the produced knit,
the chain stitch yarn of said at least one weft stitched chain stitch forming the elongate body (9) of the barbed suture and the monofilament cuts (7) extending from said weft stitches of said one weft stitched chain stitch forming the barbs (8) of said barbed suture.

23 Claims, 3 Drawing Sheets

(56) References Cited

U.S. PATENT DOCUMENTS

| | | |
|---|---|---|
| 709,392 A | 9/1902 | Brown |
| 816,026 A | 3/1906 | Meier |
| 1,188,668 A | 6/1916 | Madison |
| 2,541,499 A * | 2/1951 | Carney .................. D04B 31/00 66/202 |
| 2,541,500 A * | 2/1951 | Carney .................. D04G 3/02 66/202 |
| 3,166,072 A | 1/1965 | Sullivan, Jr. |
| 3,221,746 A | 12/1965 | Noble |
| 3,494,006 A | 2/1970 | Brumlik |
| 3,897,713 A | 8/1975 | Gugle |
| 4,015,504 A | 4/1977 | Rosan et al. |
| 4,114,624 A | 9/1978 | Haverstock |
| 4,224,946 A | 9/1980 | Kaplan |
| 4,259,959 A | 4/1981 | Walker |
| 4,517,715 A * | 5/1985 | Yoshida .................. D02G 3/42 28/144 |
| 4,647,300 A | 3/1987 | Sheets |
| 4,750,324 A * | 6/1988 | Tochacek .................. D02G 3/32 57/210 |
| 5,026,385 A | 6/1991 | Schutte et al. |
| 5,100,391 A | 3/1992 | Schutte et al. |
| 5,209,755 A | 5/1993 | Abrahan et al. |
| 5,342,376 A | 8/1994 | Ruff |
| 5,403,346 A | 4/1995 | Loeser |
| 5,403,347 A | 4/1995 | Roby et al. |
| 5,470,340 A | 11/1995 | Bezwada et al. |
| 5,502,092 A | 3/1996 | Barrows et al. |
| 5,611,986 A | 3/1997 | Datta et al. |
| 5,633,343 A | 5/1997 | Bezwada et al. |
| 5,639,851 A | 6/1997 | Bezwada et al. |
| 5,730,750 A | 3/1998 | Haradon |
| 5,769,583 A | 6/1998 | Girbinger |
| 5,797,936 A | 8/1998 | Kleihues |
| 5,834,582 A | 11/1998 | Sinclair et al. |
| 5,868,788 A | 2/1999 | Bezwada et al. |
| 5,869,597 A | 2/1999 | Newman, Jr. et al. |
| 5,951,997 A | 9/1999 | Bezwada et al. |
| 5,954,723 A | 9/1999 | Spetzler |
| 6,015,618 A * | 1/2000 | Orima ...................... D02G 3/22 428/373 |
| 6,090,908 A | 7/2000 | Jamiolkowski et al. |
| 6,102,919 A | 8/2000 | Licata |
| 6,241,747 B1 | 6/2001 | Ruff |
| 6,270,517 B1 | 8/2001 | Brotz |
| 6,289,700 B1 * | 9/2001 | Gangi ...................... D02G 3/42 28/144 |
| 6,388,043 B1 | 5/2002 | Langer et al. |
| 6,500,193 B1 | 12/2002 | Bezemer et al. |
| 6,554,840 B2 | 4/2003 | Matsutani et al. |
| 6,599,310 B2 | 7/2003 | Leung et al. |
| 6,620,178 B1 | 9/2003 | Brotz |
| 6,692,499 B2 | 2/2004 | Tormala et al. |
| 6,794,484 B2 | 9/2004 | Newman et al. |
| 6,831,149 B2 | 12/2004 | Newman et al. |
| 6,848,152 B2 | 2/2005 | Genova et al. |
| 6,991,643 B2 | 1/2006 | Saadat |
| 7,070,858 B2 | 7/2006 | Shalaby et al. |
| 7,129,319 B2 | 10/2006 | Shalaby |
| 7,225,512 B2 | 6/2007 | Genova et al. |
| 7,276,073 B2 | 10/2007 | Adams |
| 7,371,253 B2 | 5/2008 | Leung et al. |
| 7,374,566 B1 | 5/2008 | Schossau |
| 7,445,624 B2 | 11/2008 | Freier et al. |
| 7,601,164 B2 | 10/2009 | Wu et al. |
| 7,624,487 B2 | 12/2009 | Trull et al. |
| 7,681,417 B2 * | 3/2010 | Hagihara ................ D02G 3/443 66/174 |
| 7,806,908 B2 | 10/2010 | Ruff |
| 7,913,365 B2 | 3/2011 | Genova et al. |
| 7,959,641 B2 | 6/2011 | Sorensen et al. |
| 7,967,841 B2 | 6/2011 | Yuan et al. |
| 7,975,698 B2 | 7/2011 | Browning |
| 7,996,967 B2 | 8/2011 | Genova et al. |
| 7,996,968 B2 | 8/2011 | Genova et al. |
| 8,011,072 B2 | 9/2011 | Genova et al. |
| 8,015,678 B2 | 9/2011 | Genova et al. |
| 8,020,263 B2 | 9/2011 | Genova et al. |
| 8,028,387 B2 | 10/2011 | Genova et al. |
| 8,028,388 B2 | 10/2011 | Genova et al. |
| 8,032,996 B2 | 10/2011 | Trull et al. |
| 8,083,770 B2 | 12/2011 | Leung et al. |
| 8,100,940 B2 | 1/2012 | Leung et al. |
| 8,118,834 B1 | 2/2012 | Goraltchouk et al. |
| 8,161,618 B2 | 4/2012 | Maiorino et al. |
| 8,192,462 B2 | 6/2012 | Sulamanidze et al. |
| 8,273,105 B2 | 9/2012 | Cohen et al. |
| 8,551,137 B2 | 10/2013 | Cohen et al. |
| 8,888,810 B2 | 11/2014 | Hadba et al. |
| 9,011,133 B2 | 4/2015 | Marczyk et al. |
| 2001/0021861 A1 | 9/2001 | Boebel et al. |
| 2001/0022096 A1 * | 9/2001 | Orima .................... D02G 3/449 66/170 |
| 2003/0032961 A1 | 2/2003 | Pelo et al. |
| 2003/0041426 A1 | 3/2003 | Genova et al. |
| 2003/0149447 A1 | 8/2003 | Morency et al. |
| 2004/0010275 A1 | 1/2004 | Jacobs et al. |
| 2004/0069402 A1 * | 4/2004 | Zafiroglu ................ D02G 3/42 156/256 |
| 2004/0078046 A1 | 4/2004 | Barzell et al. |
| 2004/0093028 A1 | 5/2004 | Ruff |
| 2004/0226427 A1 | 11/2004 | Trull et al. |
| 2004/0237736 A1 | 12/2004 | Genova et al. |
| 2005/0065542 A1 | 3/2005 | Mansfield |
| 2005/0267531 A1 | 12/2005 | Ruff et al. |
| 2006/0095134 A1 | 5/2006 | Trieu et al. |
| 2006/0241663 A1 | 10/2006 | Rice et al. |
| 2007/0005109 A1 | 1/2007 | Popadiuk et al. |
| 2007/0005110 A1 | 1/2007 | Collier et al. |
| 2007/0038249 A1 | 2/2007 | Kolster |
| 2007/0065663 A1 | 3/2007 | Trull et al. |
| 2007/0187861 A1 | 8/2007 | Genova et al. |
| 2007/0224237 A1 | 9/2007 | Hwang et al. |
| 2007/0225761 A1 | 9/2007 | Shetty |
| 2007/0257395 A1 | 11/2007 | Lindh et al. |
| 2008/0082113 A1 | 4/2008 | Bishop et al. |
| 2008/0109021 A1 | 5/2008 | Medoff |
| 2008/0195147 A1 | 8/2008 | Stopek |
| 2008/0221618 A1 | 9/2008 | Chen et al. |
| 2008/0281357 A1 | 11/2008 | Sung et al. |
| 2008/0312688 A1 | 12/2008 | Nawrocki et al. |
| 2009/0076543 A1 | 3/2009 | Maiorino et al. |
| 2009/0112259 A1 | 4/2009 | D Agostino |
| 2009/0140012 A1 | 6/2009 | Greer, Jr. et al. |
| 2009/0143819 A1 | 6/2009 | D Agostino |
| 2009/0248066 A1 | 10/2009 | Wilkie |
| 2009/0248070 A1 | 10/2009 | Kosa et al. |
| 2009/0287245 A1 | 11/2009 | Ostrovsky et al. |
| 2010/0016810 A1 | 1/2010 | Drews et al. |
| 2010/0023055 A1 | 1/2010 | Rousseau |
| 2010/0057123 A1 | 3/2010 | D Agostino et al. |
| 2010/0084780 A1 | 4/2010 | Lindh et al. |
| 2010/0146770 A1 | 6/2010 | Morency et al. |
| 2010/0174299 A1 | 7/2010 | Viola et al. |
| 2010/0230300 A1 | 9/2010 | Hunter et al. |
| 2010/0275750 A1 | 11/2010 | Maiorino et al. |
| 2010/0298871 A1 | 11/2010 | Ruff et al. |
| 2010/0313729 A1 | 12/2010 | Genova et al. |
| 2011/0022086 A1 | 1/2011 | D Agostino et al. |
| 2011/0046668 A1 | 2/2011 | Goraltchouk et al. |
| 2011/0046669 A1 | 2/2011 | Goraltchouk et al. |
| 2011/0125188 A1 | 5/2011 | Goraltchouk et al. |
| 2011/0190815 A1 | 8/2011 | Saliman |
| 2011/0276090 A1 | 11/2011 | Berndt et al. |
| 2011/0282384 A1 | 11/2011 | Odermatt et al. |
| 2011/0282386 A1 | 11/2011 | Friedrich et al. |
| 2011/0288583 A1 | 11/2011 | Goraltchouk et al. |
| 2011/0288584 A1 | 11/2011 | Bojarski et al. |
| 2011/0319932 A1 | 12/2011 | Avelar et al. |
| 2012/0046675 A1 | 2/2012 | Bishop et al. |
| 2012/0104644 A1 | 5/2012 | Lauria |
| 2012/0118123 A1 | 5/2012 | Maiorino et al. |
| 2012/0132054 A1 | 5/2012 | Maiorino et al. |

(56) References Cited

U.S. PATENT DOCUMENTS

2012/0197294 A1     8/2012   Martin
2015/0066081 A1*   3/2015   Martin ................ D04B 21/202
                                                             606/228
2016/0310138 A1* 10/2016   Bailly ................ D04B 21/202

FOREIGN PATENT DOCUMENTS

| EP | 2529670 A1 | 12/2012 |
|---|---|---|
| WO | 03007839 A2 | 1/2003 |
| WO | 2004062459 A2 | 7/2004 |
| WO | 2007131019 A2 | 11/2007 |
| WO | 2008042992 A2 | 4/2008 |
| WO | 2008112417 A2 | 9/2008 |
| WO | 2008141034 A1 | 11/2008 |
| WO | 2008157142 A2 | 12/2008 |
| WO | 2009105663 A2 | 8/2009 |
| WO | 2009129251 A2 | 10/2009 |
| WO | 2009132284 A2 | 10/2009 |
| WO | 2009140012 A1 | 11/2009 |
| WO | 2013026682 A1 | 2/2013 |
| WO | 2014078757 A1 | 5/2014 |

\* cited by examiner

METHOD FOR FORMING A BARBED SUTURE AND THE BARBED SUTURE THUS OBTAINED

CROSS-REFERENCE TO RELATED APPLICATIONS

This application is a divisional of U.S. patent application Ser. No. 15/095,518 filed Apr. 11, 2016, which claims benefit of and priority to European Patent Application Serial No. 15305604.9 filed Apr. 22, 2015, the disclosures of each of the above-identified applications are hereby incorporated by reference in their entirety.

BACKGROUND

1. Technical Field

The present invention relates to a method for forming a barbed suture in the surgical field. The method of the invention allows producing a high quantity of barbed suture in a reduced time and in a very cost-effective way. The invention also relates to the barbed suture obtained by this method.

2. Background of Related Art

Surgical knots have been used for ages in order to anchor and allow a conventional suture, in other words a smooth suture without barbs, to perform its role in tissue reapproximation for example. Anyway, surgical knots reduce the tensile strength of conventional sutures by thinning and stretching the material forming the suture. Indeed, it is known that the weakest portion of any suture line is the knot.

Moreover, the tying of surgical knots introduces the potential of human error. A knot-secured conventional suture may create an uneven distribution of tension across the wound, with the higher tension burden placed at the knots. In addition, in minimally invasive laparoscopic surgery, the ability to quickly and properly tie surgical knots presents a challenge. The skill necessary for performing intra- or extracorporeal knot tying for laparoscopic surgery may be acquired only with practice and patience, yet surgeons need to master such a skill in order to properly perform closure procedures. Laparoscopic knot tying is also more mentally and physically stressful on surgeons.

Given the excessive relative wound tension on the knot and the reasonable concerns of surgeons for suture failure due to knot slippage, there is a natural tendency toward overcoming these potential issues by over-tightening knots. However, tighter knots may be worse for wound healing and strength than looser knots. Surgical knots, when tied too tightly, can cause localized hypoxia, reduced fibroblast proliferation, and excessive tissue overlap, leading to reduced strength in the healed wound.

Eventually, a surgical knot yields the highest density of foreign body material in any given suture line and the volume of a knot may be directly related to the total amount of surrounding inflammatory reaction. If minimizing the inflammatory reaction in a wound is important for optimized wound healing, then minimizing knots sizes or even eliminating knots altogether would be beneficial as long as the wound-holding strength of the suture line is not compromised.

For all these reasons, the use of barbed suture, suture with barbs, has tremendously increased in the past years. In particular, one of the most costly parts of a surgical procedure is time in the operating room. With rising healthcare costs, efficiency in the operating room is becoming more of a priority. Significantly faster closure times have been observed with the use of knotless barbed sutures. The use of knotless barbed suture can securely reapproximate tissues with less time, cost, and risks.

Barbed sutures are known. They basically consist in strands of smooth suture provided with barbs on their surfaces. Barbed sutures are generally made of the same materials as conventional sutures and offer several advantages for closing wounds compared with conventional sutures. A barbed suture includes an elongated body that has one or more spaced barbs, that project from the surface of the suture body along the body length.

The barbs are generally arranged to allow passage of the barbed suture in one direction through tissue but resist movement of the barbed suture in the opposite direction (one-way suture). One advantage of barbed sutures is the provision of a non-slip property. Barbed sutures are known for use in cosmetic, laparoscopic and endoscopic procedures. The number of barbs needed for a particular suture may be influenced by the size of the wound and the strength required to hold the wound closed. Like a conventional suture, a barbed suture may be inserted into tissue using a surgical needle.

In some circumstances, a random configuration of barbs on the exterior surface of the suture is preferred to achieve optimal holding of the wound closure for a particular wound. However, in other circumstances, where the wound or tissue repair needed is relatively small, a reduced number of barbs may be desired.

Various methods of forming barbs on sutures have been proposed such as mechanical cutting, laser cutting, injection molding, stamping, extrusion and the like. However, such methods may be difficult or costly, in particular when a specific arrangement or configuration of barbs is needed for an appropriate surgical procedure.

For example, conventional cutting methods of forming barbs may involve cutting with a blade into the elongate body of the suture, where the elongate body may be a monofilament for example. Barbed sutures may be fabricated from monofilament fibers by a micro-machining technique, which escapes barbs into the fiber around the circumference in a variety of configurations. Cutting methods have therefore significant drawbacks as they weaken the core of the suture and narrow its functional diameter. Moreover, they are costly and have slow manufacturing cycle time.

Accordingly, there is a continuous need for methods of forming barbs on a suture that are less difficult to implement, more efficient and cost effective. There is also a continuous need for methods allowing varying the size, the location and the depth of the barbs, as well as the amount of barbs present on the suture, depending on the contemplated surgical application.

SUMMARY

A first aspect of the invention is a method for forming a barbed suture comprising an elongate body provided with barbs extending substantially radially out from said elongate body, said method comprising the following steps:

a) producing a knit on a warp knitting machine comprising at least two guide bars, a first guide bar B1 and a second guide bar B2, by knitting together i) a set of chain stitch yarns of a first biocompatible material threaded in said first guide bar B1 and producing chain stitches and ii) a set of monofilament weft yarns of a second biocompatible material threaded in said second guide bar B2, the knitting pattern followed by the second guide bar B2 producing at least a partial weft in which said monofilament weft yarns complete weft stitches with at least one of said chain stitches, thereby producing at least one weft stitched chain stitch, b) cutting the knit along the warp direction on both sides of said at least one weft stitched chain stitch, so as to isolate said weft stitched chain stitch from the rest of the produced knit, the chain stitch yarn of said at least one weft stitched chain stitch forming said elongate body of said barbed suture and the monofilament cuts extending from said weft stitches of said at least one weft stitched chain stitch forming said barbs of said barbed suture.

The barbed suture obtained by the method of the invention therefore comprises an elongate body made of a yarn of a first biocompatible material, provided with barbs extending substantially radially out from said elongate body, said barbs being monofilament cuts made of a second biocompatible material, where said monofilament cuts are stitched to said yarn forming said elongate body. Another aspect of the invention is a barbed suture comprising an elongate body made of a yarn of a first biocompatible material, provided with barbs extending substantially radially out from said elongate body, said barbs being monofilament cuts made of a second biocompatible material, where said monofilament cuts are stitched to said yarn forming said elongate body, said barbed suture being obtained by the method above.

In a first step, step a), of the method of the invention, a knit is produced on a warp knitting machine comprising at least two guide bars, a first guide bar B1 and a second guide bar B2, by knitting together i) a set of chain stitch yarns of a first biocompatible material threaded in said first guide bar B1 and producing chain stitches and ii) a set of monofilament weft yarns of a second biocompatible material threaded in said second guide bar B2, the knitting pattern followed by the second guide bar B2 producing at least a partial weft in which said monofilament weft yarns complete weft stitches with at least one of said chain stitches, thereby producing at least one weft stitched chain stitch.

The warp knitting machine may be for example a crochet machine or a raschel knitting machine. Warp knitting machines have a warp yarn for each needle.

By "chain stitch" is meant according to the present application a stitch construction where both over and under-lapping are always carried out across the same needle. One chain stitch of a knit therefore involves only one warp yarn, in other words involves only one yarn in the warp direction. The tensile strength of one chain stitch is therefore the tensile strength of said single warp yarn involved in the construction of the chain stitch.

The method of the invention allows producing barbed sutures in a very simple, easy and rapid process. In particular the method of the invention is a cost effective process as there is no need to use sophisticated cutting machines with blades for performing cuts into the body of a monofilament.

It is known that warp knitting machines are capable of producing knits at high production rates. In addition, the knits produced may also show a very long dimension along the warp direction, which is the direction of manufacturing the knit.

As an example, with current existing warp knitting machines, knits of at least 300 meters long may be produced. The method of the invention therefore allows manufacturing a barbed suture of 300 meters long in a very cost effective way, and in particular in only one knitting step.

In addition, the barbs created in the barbed suture produced according to the method for the invention are ineradicable since they are made of monofilament cuts that stitch through chain stitches pillar.

In embodiments, the knitting pattern followed by the second guide bar B2 produces at least a partial weft in which said monofilament weft yarns complete weft stitches with a plurality of chain stitches, thereby producing a plurality of weft stitched chain stitches, and wherein the cutting of step b) is repeated for each weft stitched chain stitch, thereby producing a plurality of barbed sutures.

The method of the invention therefore allows manufacturing simultaneously a plurality of barbed sutures of significant length each.

In current existing warp knitting machines, a high number of chain stitches may be produced along the width of a knit. As an example, 286 or more chain stitches may be produced on the width of a knit. If the knit produced is 300 meters long, this means that at least 85 800 meters of barbed suture may be produced in one single knitting step with the method of the invention. The time needed for producing such 85 800 meters of barbed suture may range for example from 30 hours to 60 hours. In other words, the method of the invention allows producing for example 10 meters of barbed suture per hour.

Guide bar B2 may be fed continuously or intermittently with the monofilament weft yarns during step a). In embodiments, guide bar B2 is fed continuously with the monofilament weft yarns during step a). The method of the invention further allows producing a barbed suture having different functional portions along its length. In particular, the method of the invention allows producing barbed suture having active portions, namely portions provided with barbs, and passive portions, namely portions free of any barbs. The passive portions may be obtained by simply stopping the feeding of the second guide bar B2 with the weft yarns for a certain period of time during the knitting process of step a°) of the method of the invention. Barbed sutures having alternating active portions and passive portions may therefore be obtained by simply intermittently feeding the second guide bar B2 during the knitting process. In embodiments, the second guide bar B2 is fed intermittently with said set of monofilament weft yarns.

Alternatively, barbed sutures having alternating active portions and passive portions may be obtained by modifying the knitting pattern of guide bar B2 so that, for one or several determined time periods during step a) of production of the knit, the monofilament weft yarns do not complete any weft stitches with said weft stitched chain stitch(es).

The method of the invention further allows varying and selecting the length of the barbs according to an easy process. Indeed, the length of the barbs of the barbed sutures obtained with the method of the invention will be dependent first on the distance left between a weft stitched chain stitch and the two adjacent chain stitches on both sides of said weft stitched chain stitch, said distance being a function of the knitting pattern, and second on the location of the cutting line on said distance at the time of the cutting step b) of the method of the invention. The distance left between a weft stitched chain stitch and the two adjacent chain stitches will be function of the threading-in of the two guide bars, in particular of the threading-in of the first guide bar B1 forming the chain stitches. The greater the distance desired, the more empty needles left between two full needles. On the contrary, the smaller the distance desired between two adjacent weft stitched chain stitches, the less empty needles left between two full needles.

In embodiments, the first guide bar B1 is threaded 1 full, 3 empty. Alternatively, the first guide bar B1 may be threaded 1 full, 4 empty, or 1 full, 5 empty.

In embodiments, the knitting pattern followed by bars B1 and B2 is the following according to the ISO 11676 standard:
Bar B1: 0.1/0.1/1.0/1.0//
B2: 0.0/4.5/9.9/5.4//
wherein B1 is threaded 1 full, 3 empty, and B2 is threaded 1 full, 7 empty, along the whole width of the machine.

Such a pattern results in a distance between a weft stitched chain stitch and the two adjacent chain stitches of about 5 mm.

In other embodiments, the knitting pattern followed by bars B1 and B2 is the following according to the ISO 11676 standard:
Bar B1: 0.1/1.0//
Bar B2: 9.9/5.4/0.0/0.0/4.5/9.9//
wherein B1 is threaded 1 full, 3 empty, and B2 is threaded 1 full, 7 empty, along the whole width of the machine.

Such a pattern results in a distance between a weft stitched chain stitch and the two adjacent chain stitches of about 5 mm.

The method of the invention also allows varying and selecting the amount or number of barbs along the length of the suture in an easy way. In particular, the method of the invention allows selecting a specific frequency of barbs along the length of the suture, in other words a number of barbs per centimeter of suture. Such a frequency will depend on the knitting pattern followed by the second guide B2 threaded with the monofilament weft yarns. In particular, the more weft stitches completed along the warp direction of the chain stitch, the more weft stitches present on the isolated weft stitched chain stitch in the end, and the higher the frequency of barbs on the resulting barbed suture. In embodiments, the knitting pattern followed by the second guide bar B2 produces a partial weft in which said monofilament weft yarns complete from about 4 to about 15 weft stitches/cm along a length of each said weft stitched chain stitch.

In addition, the method of the invention allows producing barbed sutures without affecting the tensile strength of the elongate body of the barbed suture. Indeed, contrary to cutting methods of the prior art which create the barbs by performing cuttings in the elongate body of the suture, made of a monofilament for example, the method of the invention leaves the yarn forming the elongate body of the suture integrate. The integrity of the yarn is not affected. As a consequence, the tensile strength of the yarn forming the elongate body of the barbed suture obtained by the method of the invention is not affected by the presence of the barbs. Moreover, the method of the invention allows using both monofilaments and multifilaments yarns as the elongate body of the suture, whereas the methods involving cutting steps request that the elongate body be a unitary structure, such as a monofilament yarn.

In embodiments, the chain stitch yarns, that will form the elongate body of the barbed suture, may be monofilaments or multifilaments. In embodiments, the chain stitch yarns are monofilaments yarns, for example having a diameter ranging from about 0.07 mm to about 0.3 mm. In embodiments, the chain stitch yarns are multifilaments. Existing multifilament yarns may show high tenacity, in other words, high tensile strength. In embodiments, the chain stitch yarns may be multifilament yarns having a tensile strength ranging from about 25 cN/dTex to about 40 cN/dTex, for example a tensile strength of about 35 cN/dTex.

The method of the invention allows producing barbed sutures with barbs having varying surface area in a very easy way. In particular, the size and/or the surface area of the barbs of the suture obtained by the method of the invention will be dependent on the size of the diameter of the monofilament weft yarns. In embodiments, the monofilament weft yarns show a diameter ranging from 0.07 mm to 0.3 mm. Such a diameter allows obtaining a good fixation of the barbed suture within the biological tissues.

Barbs of varying size may be desired depending on the contemplated surgical application. For joining fat and relatively soft tissues, larger barbs may be desired, whereas smaller barbs may be more suitable for collagen-dense tissues. With the method of the invention, the production of small or alternatively large barbs may be easily obtained by simply selecting monofilament weft yarns of adequate diameters. For example, for obtaining a barbed suture with large barbs according to the method of the invention, monofilament weft yarns with a diameter ranging from 0.2 mm to 0.3 mm may be used. In embodiments, the monofilament weft yarns may show a diameter ranging from 0.2 mm to 0.3 mm. Alternatively, for obtaining a barbed suture with small barbs according to the method of the invention, monofilament weft yarns with a diameter ranging from 0.07 mm to 0.1 mm may be used. In embodiments, the diameter of the monofilament weft yarn may range from 0.07 mm to 0.1 mm.

In some embodiments, a combination of large and small barbs within the same suture may be desirable, for example when a suture is used in tissue repair with differing layer structures. Use of the combination of large and small barbs with the same suture wherein barb sizes are customized for each tissue layer will ensure maximum anchoring properties. In embodiments, the barbed suture obtained by the method of the invention may have both large and small barbs. Such a barbed suture with a combination of large and small barbs may be obtained with a warp knitting machine including a third guide bar B3, where a first set of monofilament weft yarns of a large diameter, for example ranging from 0.20 mm to 0.25 mm, is threaded on the second guide bar B2, and a second set of monofilament weft yarns of a small diameter, for example ranging from 0.07 mm to 0.09 mm, is threaded on the third guide bar B3.

The barbed suture obtained by the method of the invention is formed of an elongate body made from a chain stitch yarn formed of a first biocompatible material, and of barbs made of monofilaments cuts originating from monofilament weft yarns formed of a second biocompatible material. The first biocompatible material and the second biocompatible material may be identical or different. In embodiments, the first biocompatible material and the second biocompatible material are identical, and the chain stitch yarn and the monofilament weft yarns are therefore made of the same material. In other embodiments, the first biocompatible material and the second biocompatible material are different, and the chain stitch yarn and the monofilament weft yarns are therefore made of different materials.

The first biocompatible material and the second biocompatible material may be synthetic or natural. The first and second biocompatible polymer materials may be biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

The first and second biocompatible materials may be selected from the group consisting of biodegradable polymers, non-biodegradable polymers, and combinations thereof.

Non-biodegradable materials that may be used as first biocompatible material and second biocompatible material of the method of the invention include polyolefins, such as polyethylene, polypropylene, copolymers of polyethylene and polypropylene, and blends of polyethylene and polypropylene; polyamides (such as nylon); polyamines, polyimines, polyesters such as polyethylene terephthalate; polytetrafluoroethylene; polyether-esters such as polybutester; polytetramethylene ether glycol; 1,4-butanediol; polyurethanes; and combinations thereof. In other embodiments, non-degradable materials may include silk, collagen, cotton, linen, carbon fibers, titanium, and the like. The polypropylene may be isotactic polypropylene or a mixture of isotactic and syndiotactic or atactic polypropylene.

Biodegradable materials that may be used as first biocompatible material and second biocompatible material of the method of the invention include polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), copolymers of these materials and mixtures thereof.

In embodiments, the first biocompatible material and the second biocompatible material are each selected from polyethylene, polypropylene, polyester such as polyethylene terephthalates, polyamide, silicone, polyether ether ketone (PEEK), polyarylether ether ketone (PAEK), polylactic acid (PLA), polycaprolactone (PCL), polydioxanone (PDO), trimethylene carbonate (TMC), polyvinyl alcohol (PVA), polyhydroxyalkanoate (PHA), polyglycolic acid (PGA), copolymers of these materials, and mixtures thereof.

In embodiments, the first biocompatible material is polyethylene. The polyethylene may be a ultra high molecular weight polyethylene conferring to a multifilament yarn made therefrom a high tensile strength. In embodiments, the chain stitch yarns may be polyethylene multifilament yarns having a tensile strength ranging from about 25 cN/dTex to about 40 cN/dTex, for example a tensile strength of about 35 cN/dTex. Such polyethylene multifilament yarns made from ultra high molecular weight polyethylene and provided with such a tensile strength are commercially available from the company DSM under the tradename "Dyneema Purity®.

In embodiments, the first biocompatible material is polyethylene terephthalate. In embodiments, the chain stitch yarns may be polyethylene terephthalate multifilament yarns having a tensile strength ranging from about 25 cN/dTex to about 40 cN/dTex, for example a tensile strength of about 35 cN/dTex.

In embodiments, the second biocompatible material is polypropylene. Polypropylene may confer rigidity to the weft monofilaments and therefore to the barbs obtained therefrom.

The method of the invention allows customizing the elongate body and the barbs of the barbed suture in function of the contemplated surgical application. For example, if the barbed suture is to be used to connect the edges of a wound in skin or tendon, the barbs may be made relatively short and more rigid, for example by using polypropylene monofilament weft yarns, to facilitate entry into this rather firm tissue. Alternatively, if the barbed suture is intended for use in fatty tissue, which is relatively soft, the barbs may be made longer and spaced further apart to increase the ability of the suture to grip the soft tissue.

In a second step, step b), of the method of the invention, the knit produced in step a) is cut along the warp direction on both sides of said at least one weft stitched chain stitch, so as to isolate said weft stitched chain stitch from the rest of the produced knit. In embodiments where the knitting pattern followed by the second guide bar B2 produces at least a partial weft in which said monofilament weft yarns complete weft stitches with a plurality of chain stitches, thereby producing a plurality of weft stitched chain stitches, the cutting of step b) is repeated for each weft stitched chain stitch, thereby producing a plurality of barbed sutures. For each such isolated weft stitched chain stitch, the chain stitch yarn will form the elongate body of the thus obtained barbed suture and the monofilament cuts extending from the weft stitches of the weft stitched chain stitch will form the barbs of the thus obtained barbed suture.

In embodiments, the cutting step may be performed on line, namely while the knit produced at step a) is still on the knitting machine. For example, the knitting machine may be provided with adequate blades. Alternatively, the cutting step may be performed off line, for example with pairs of scissors.

In embodiments, the cutting step may be performed via melting the weft monofilaments at a temperature above their melting point so as to cut said monofilaments. Such a cutting step may be performed on line or off line.

After cutting step b) of the method of the invention, the monofilament cuts forming the barbs may generally extend substantially radially out of the chain stitch yarn forming the elongate body of the barbed suture along an angle between the monofilaments cuts and the chain stitch yarn of about 90°. In the present application, the angle between the monofilament cuts and the yarn forming the elongate body is measured with a Profile Projector ORAM 300 V geometric.

The angle between the monofilament cuts and the yarn forming the elongate body may be modified by submitting the isolated weft stitched chain stitch to a stretching treatment. For example, the angle between the monofilament cuts and the yarn forming the elongate body may be modified so that said angle reaches 45°, 35°, or 33°. The method of the invention therefore allows selecting the adequate angle between the barbs and the elongate body of the barbed suture for an optimized fixation in the biological tissues.

In embodiments, the method further comprises a stretching step during which either the knit produced in step a) or the isolated weft stitched chain stitch resulting from step b) is submitted to a stretching treatment. The stretching treatment may comprise a step of stretching the knit in the warp direction or stretching the isolated weft stitched chain stitch in the direction of its length, in other words in the warp direction. For example, in the case of an isolated weft stitched chain stitch, the stretching treatment may be performed by using a traction testing machine such as Hounsfield model H5KS in which a first end of the isolated weft stitched chain stitch is grasped by a fixed jaw of the machine and the opposite end of the isolated weft stitched chain stitch is grasped by a moving jaw. By moving away from the fixed jaw, the moving jaw stretches the isolated weft stitched chain stitch.

On a industrial scale, the stretching treatment of the knit in the warp direction may be performed on a heat-setting machine for example. By stretching the knit in the warp direction, all weft stitched chain stitch(es) of the knit are stretched.

In embodiments, the weft stitched chain stitch, isolated or not, is stretched from about 0% to about 90%, which means that the stretched weft stitched chain stitch shows a length from about 0% to about 90% greater than the initial length of the weft stitched chain stitch.

In embodiments, the weft stitched chain stitch, isolated or not, is stretched at 40%, which means that the stretched weft stitched chain stitch shows a length 40% greater than the initial length of the weft stitched chain stitch. Such a stretching step of 40% may result in the angle between the monofilament cuts and the yarn forming the elongate body be modified to reach about 45°. Such an angle between the monofilament cuts and the yarn forming the elongate body of the barbed suture may be desirable for barbed sutures intended to be used in soft biological tissues.

In other embodiments the weft stitched chain stitch, isolated or not, is stretched at 80%, which means that the stretched weft stitched chain stitch shows a length 80% greater than the initial length of the weft stitched chain stitch. Such a stretching step of 80% may result in the angle between the monofilament cuts and the yarn forming the elongate body be modified to reach about 35°. Such an angle between the monofilament cuts and the yarn forming the elongate body of the barbed suture may be desirable for barbed sutures intended to be used for anchoring purposes in dense biological tissues such as muscles.

In other embodiments the weft stitched chain stitch, isolated or not, is stretched at 90%, which means that the stretched weft stitched chain stitch shows a length 90% greater than the initial length of the weft stitched chain stitch. Such a stretching step of 90% may result in the angle between the monofilament cuts and the yarn forming the elongate body be modified to reach about 33°. Such an angle between the monofilament cuts and the yarn forming the elongate body of the barbed suture may be desirable for barbed sutures intended to be used for anchoring purposes in dense biological tissues such as muscles.

In embodiments, the isolated weft stitched chain stitch may be submitted to a twisting treatment, for example for giving to the barbs a helical pattern. Such a treatment may be performed with a rotor machine.

In embodiments, the method of the invention further comprises a heat-setting step during which either the knit produced in step a) or the isolated weft stitched chain stitch resulting from step b) is submitted to a heat-setting treatment. The heat-setting treatment is intended to fix the barbed suture in the desired configuration. The heat-setting step may take place either between step a) and b), namely before the cutting step, or after step b), namely after the cutting step. For example, in case the knit or the isolated weft stitched chain stitch is submitted to a stretching treatment and/or a twisting treatment, it may simultaneously be submitted to a heat-setting treatment, so that the barbs configuration regarding for example the angle made between the monofilaments cuts and the elongate body and/or the helical pattern obtained by the twisting treatment are fixed.

The heat-setting treatment may comprise a step of heating the knit or the isolated weft stitched chain stitch at a temperature ranging from 30° C. to 230° C. during a time period ranging from 1 min to 4 min. The heat-setting treatment may be performed on a heat-setting machine.

The barbed suture obtained by the method of the invention may be sterilized by any means within the purview of those skilled in the art.

The barbed suture obtained by the method of the invention may be coated or impregnated with one or more medico-surgically useful substances which accelerate or beneficially modify the healing process when the barbed suture is applied to a wound or surgical site. In certain embodiments, the coating may be formed from biodegradable polymers selected from the group consisting of lactones, carbonates, polyorthoesters, hydroxyalkoanates, hydroxybutyrates, bioactive agents, polyanhydrides, silicone, calcium stearoyl lactylates, vinyl polymers, high molecular weight waxes and oils, natural polymers, proteins, polysaccharides, suspendable particulates, dispersible particulates, microspheres, nanospheres, rods, homopolymers thereof, copolymers thereof, and combinations thereof.

Suitable bioactive agents include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents include substances which are beneficial and tend to promote the healing process. For example, a barbed suture obtained by the method of the invention can be provided with a bioactive agent that will be deposited at the sutured site. The bioactive agent can be chosen for its antimicrobial properties, capability for promoting wound repair and/or tissue growth, or for specific indications such as thrombosis.

The barbed suture obtained by the method of the invention may additionally comprise a needle at one end. Two tipped ends of the barbed suture may be desirable for attaching a needle to each end of the suture to provide a so-called double armed suture. The needle attachment may be made by any conventional method such as crimping, swaging, and the like. In some cases, a tubular insertion device (not shown) may be utilized to introduce a barbed suture obtained by the method of the invention into tissue.

The barbed suture obtained by the method of the invention may be utilized in any cosmetic, orthopedic, open endoscopic or laparoscopic methods. In addition, barbed sutures obtained by the method of the invention may be utilized to attach one tissue to another including, but not limited to, attaching tissue to a ligament. Specific applications of cosmetic surgeries include, for example, facelifts, browlifts, thigh lifts, and breast lifts. The barbed suture obtained by the method of the invention may further be used as a device for occlusion of a corporeal duct, for example for closing a varicose vein.

BRIEF DESCRIPTION OF THE DRAWINGS

The advantages of the method of the invention will appear more clearly from the following examples and attached drawings in which.

DETAILED DESCRIPTION OF THE EMBODIMENTS

Examples

Example 1

A knit is produced on a raschel machine wherein the knitting pattern followed by bars B1 and B2 is the following according to the ISO 11676 standard:
Bar B1: 0.1/0.1/1.0/1.0//
Bar B2: 0.0/4.5/9.9/5.4//
wherein B1 is threaded 1 full, 3 empty, and B2 is threaded 1 full, 7 empty.

The yarns threaded in guide bar Bar 1 are multifilament yarns of ultra high molecular weight polyethylene, such as those marketed by the company DSM under the tradename "Dyneema Purity®". These multifilaments have a tensile strength of 35 cN/dTex.

The monofilaments threaded in guide bar Bar 2 are polypropylene monofilaments having a diameter of 0.25 mm.

Figure 1:
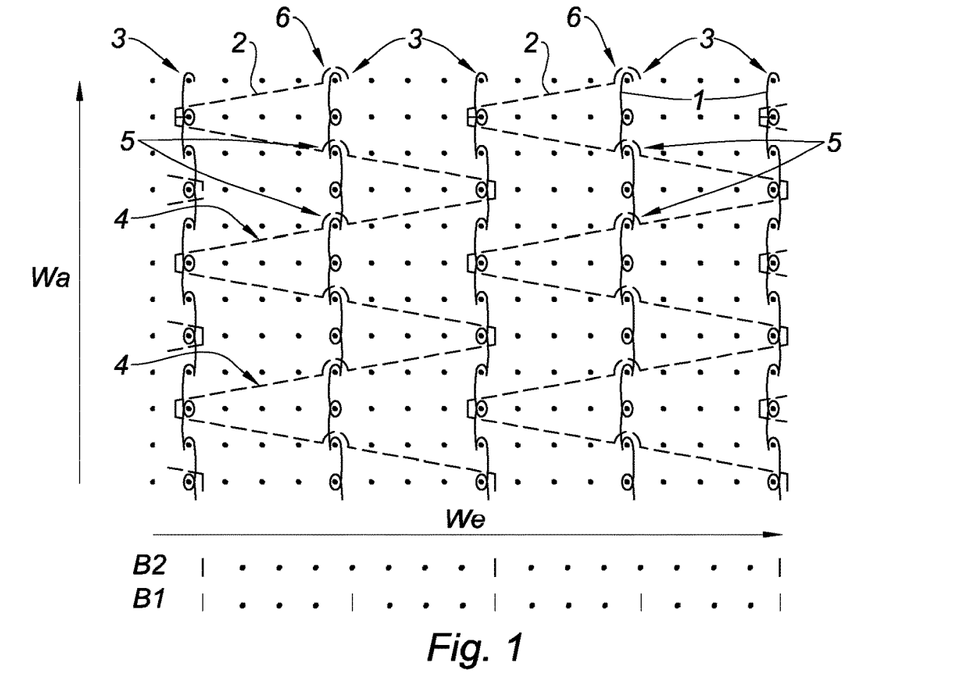
FIG. 1 is a schematic view showing a first embodiment of a knitting pattern suitable for the knitting process of step a°) of the method of the invention.

With reference to FIG. 1 showing the knitting pattern above in accordance with a representation well known for one skilled in the art, are shown the warp direction Wa, the weft direction We, the chain stitch yarns 1 (threaded in guide bar B1) and the monofilament weft yarns 2 (threaded in guide bar B2). The knitting pattern produces a plurality of chain stitches 3 and a partial weft 4. The weft yarns 2 complete weft stitches 5 with some of the chain stitches 3, herein after called weft stitched chain stitches 6. Actually, as appears from FIG. 1, the knitting pattern produces one weft stitched chain stitch 6 out of two chain stitches 3 present in the knit. In the present example, the distance between two adjacent weft stitched chain stitches 6 is due to the threading-in of the first guide bar B1, which is 1 full, 3 empty. Such a threading-in may result in a distance between the weft stitched chain stitches 6 of about 0.5 cm.

Figure 3:
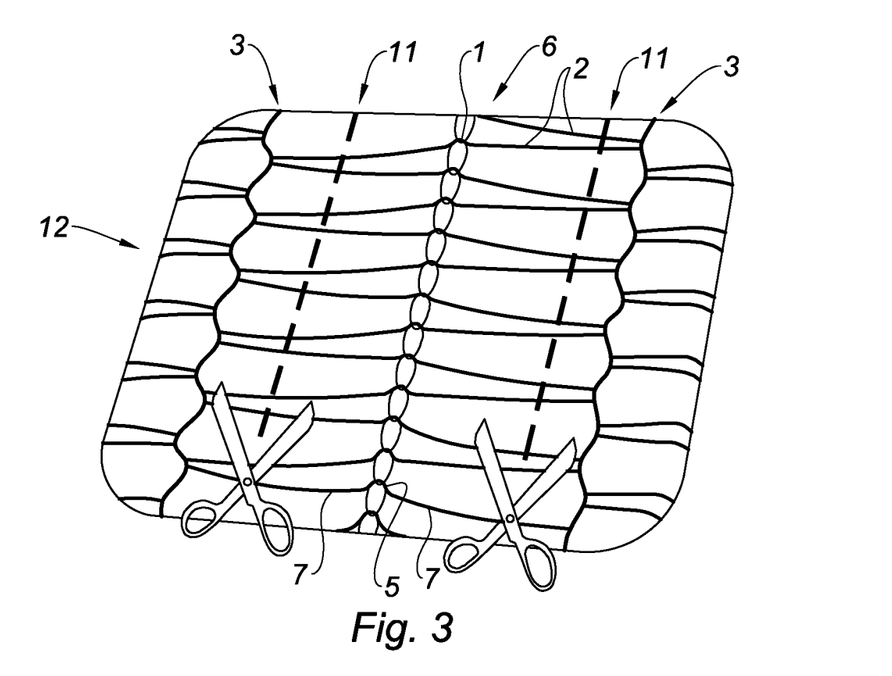
FIG. 3 is a schematic view showing the cutting step of the method of the invention.

With reference to FIG. 3, is shown schematically a piece of knit 12 produced with the pattern of FIG. 1.

Once the knit is produced, it is cut along the warp direction on both sides of the weft stitched chain stitches 6 along cutting lines 11 as shown on FIG. 3. The cutting step may be performed for example with a pair of scissors.

Figure 4:
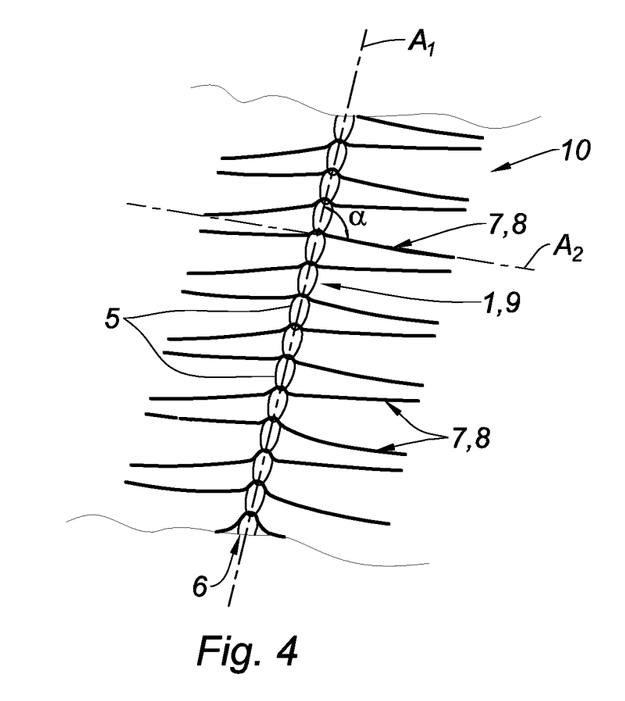
FIG. 4 is a front view showing a barbed suture obtained by the method of the invention.

An isolated weft stitched chain stitch 6, in which the chain stitch yarn 1 of the weft stitched chain stitch 6 forms the elongate body 9 of a barbed suture 10 and the monofilament cuts 7 extending from the weft stitches 5 of the weft stitched chain stitch 6 form the barbs 8 of the barbed suture 10 is obtained, as shown on FIG. 4. As shown on this Figure, the weft stitched chain stitch 6 which is also the elongate body 9 of the suture 10 extends along a longitudinal axis A1, and the monofilament cuts 7, which are also the barbs 8, each extend along a longitudinal axis A2. On FIG. 4, which shows the isolated weft stitched chain stitch 6 right after the cutting step, the angle α between axis A1 and axis A2 is substantially about 90°.

As appears from the cutting step shown on FIG. 3, the length of the monofilament cuts 7, and therefore of the barbs 8, depend both on the initial distance between the weft stitched chain stitch 6 and adjacent chain stitches 3, and on the location of the cutting lines 11.

Figure 6:
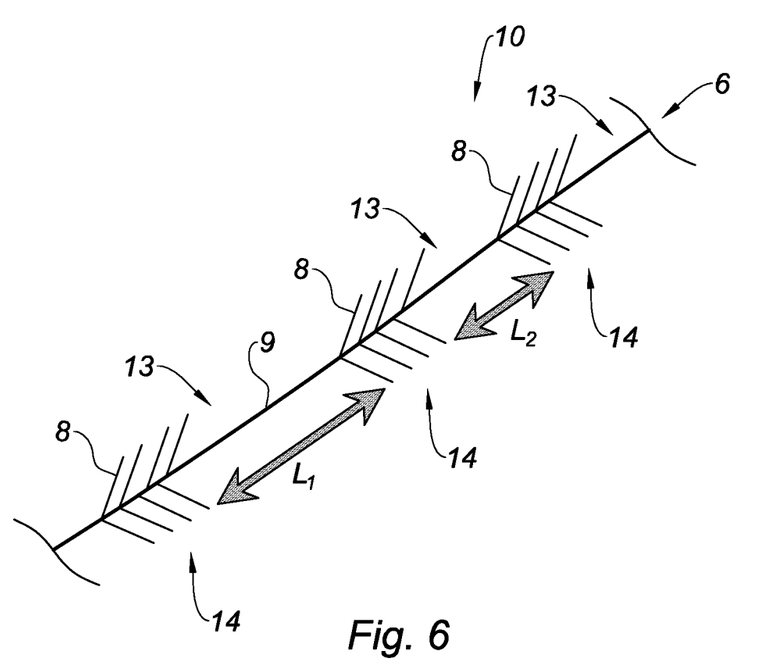
FIG. 6 is a partial schematic view of a barbed suture obtained by the method of the invention having active and passive portions along its length.

With reference to FIG. 6 is shown schematically a barbed suture 10 obtained according to the method of the present example in the case where the second guide bar B2 was fed intermittently with the set of monofilament weft yarns. During the time periods for which the guide bar B2 was not fed with the monofilament weft yarns, no weft stitches were produced on the weft stitched chain stitch 6, thereby resulting in portions of the weft stitched chain stitch 6 free of barbs, namely passive portions 13. A barbed suture 10 having alternating active portions 14 (when guide bar B2 was fed with monofilament wefts yarns) and passive portions 13 is therefore be obtained. As shown on this Figure, the respective distances (L1, L2) between two adjacent active portions 14 may vary, as such distances are dependent on the time period during which the guide bar B2 was not fed.

Figure 5:
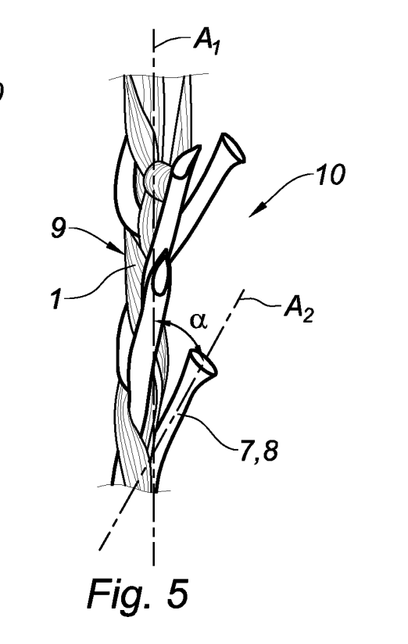
FIG. 5 is a partial front view of a barbed suture obtained by the method of the invention showing the angle formed between the monofilament cuts and the yarn forming the elongate body.

With reference to FIG. 5 is shown a larger view of the barbed suture 10 of FIG. 4 after a stretching treatment in which the barbed suture was stretched at 90%. As appears from this Figure, after the stretching treatment, the angle α between axis A1 and axis A2, in other words between the multifilament yarn 1 forming the elongate body 9 of the barbed suture 10 and the monofilament cuts 7, also barbs 8, has been modified and is now about 33°.

The barbed suture 10 of FIG. 5 is then submitted to a heat-setting treatment in order to fix the configuration of the barbs 8 with respect to the elongate body 9 of the suture 10.

In embodiments not shown, the knitting pattern may result in all chain stitches being also weft stitched chain stitches, when the weft yarns produce weft stitches with all chain stitches produced by the first guide bar. In other embodiments, the knitting pattern may produce only one weft stitched chain stitch out of three, four, five, etc . . . chain stitches present in the knit, which may result in variations of the distance between two adjacent weft stitched chain stitches. Alternatively, this distance may vary due to different threading-in of the guide bars.

Example 2

In this example is described an alternative knitting pattern to Example 1 for producing a barbed suture of the invention.

A knit is produced on a raschel machine wherein the knitting pattern followed by bars B1 and B2 is the following according to the ISO 11676 standard:
Bar B1: 0.1/1.0//
Bar B2: 9.9/5.4/0.0/0.0/4.5/9.9//
wherein B1 is threaded 1 full, 3 empty, and B2 is threaded 1 full, 7 empty.

The yarns threaded in guide bar Bar 1 are multifilament yarns of ultra high molecular weight polyethylene, such as those marketed by the company DSM under the tradename "Dyneema Purity®". These multifilaments have a tensile strength of 35 cN/dTex.

The monofilaments threaded in guide bar Bar 2 are polypropylene monofilaments having a diameter of 0.25 mm.

Figure 2:
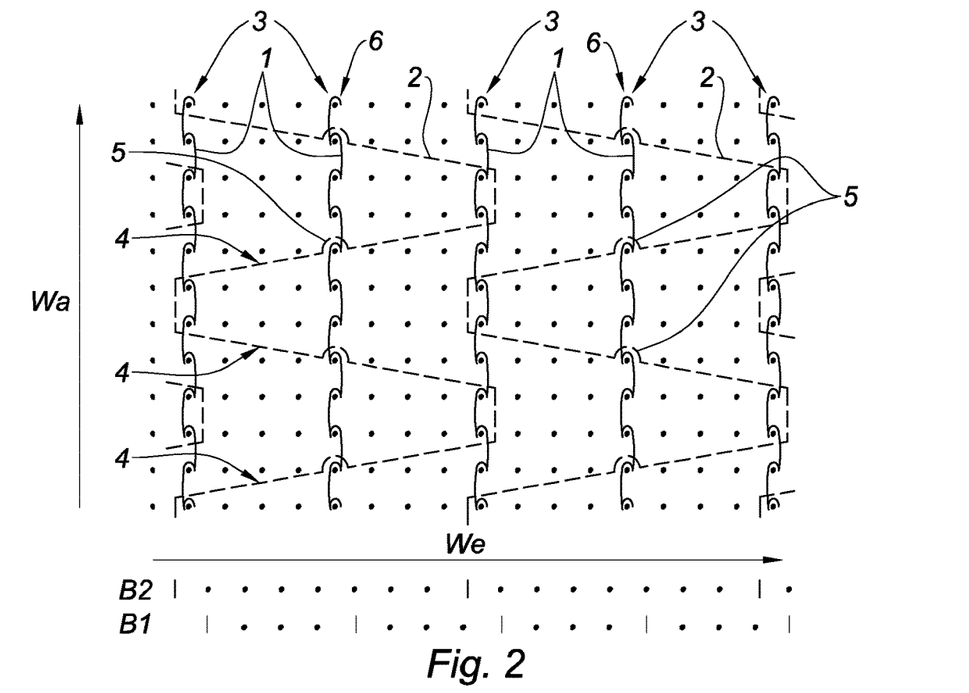
FIG. 2 is a schematic view showing a second embodiment of a knitting pattern suitable for the knitting process of step a°) of the method of the invention.

With reference to FIG. 2 showing the knitting pattern, are shown the chain stitch yarns 1 (threaded in guide bar B1) and the monofilament weft yarns 2 (threaded in guide bar B2). The knitting pattern produces a plurality of chain stitches 3 and a partial weft 4. The weft yarns 2 complete weft stitches 5 with some of the chain stitches 3, herein after called weft stitched chain stitches 6. Actually, as appears from FIG. 2, the knitting pattern produces one weft stitched chain stitch 6 out of two chain stitches 3 present in the knit. In the present example, the distance between two adjacent weft stitched chain stitches 6 is due to the threading-in of the first guide bar B1, which is 1 full, 3 empty. Such a threading-in may result in a distance between the weft stitched chain stitches 6 of about 0.5 cm.

Once the knit is produced, it is cut as described in Example 1 to obtain an isolated weft stitched chain stitch 6.

The isolated weft stitched chain stitch 6 may then be stretched, and/or twisted in order to put the monofilaments cuts 7, also barbs 8, in a desired configuration, and eventually heat-set in order to fix said configuration to obtain a barbed suture 10 of the invention.

The method of the invention allows adapting very easily and in a cost effective manner the nature and structure of the barbed suture, such as frequency per cm, configuration, spacing, length and surface area of the barbs, depending upon the tissue in which the barbed suture is to be used. With the method of the invention, it is possible to obtain a barbed suture in which the barbs may be arranged in any suitable pattern, for example, helical, linear, or randomly spaced. In addition, the method of the invention allows producing a high amount of barbed suture in a cost effective way and at high production rates.

What is claimed is:

1. A barbed suture comprising an elongate body made of a yarn of a first biocompatible material, provided with barbs extending substantially radially out from said elongate body, said barbs being monofilament cuts made of a second biocompatible material, where said monofilament cuts are stitched to said yarn forming said elongate body.

2. The barbed suture of claim 1, wherein the elongate body comprises a plurality of chain stitches formed from chain stitch yarns.

3. The barbed suture of claim 2, wherein the chain stitch yarns are monofilament yarns.

4. The barbed suture of claim 2, wherein the chain stitch yarns are multifilament yarns.

5. The barbed suture of claim 4, wherein the multifilament chain stitch yarns have a tensile strength ranging from about 25 cN/dTex to about 40 cN/dTex.

6. The barbed suture of claim 2, wherein at least one of the chain stitches is combined with a weft stitch of a weft yarn to form a weft stitched chain stitch along the elongate body.

7. The barbed suture of claim 6, wherein the chain stitch of the weft stitched chain stitch forms the elongate body and the monofilament cuts are formed from the weft stitch of the weft stitched chain stitch.

8. The barbed suture of claim 6, wherein the chain stitch yarns are polyethylene multifilament yarns having a tensile strength of about 35 cN/dTex and the weft yarns are polypropylene monofilaments.

9. The barbed suture of claim 6, wherein the weft stitched chain stitch is heat-set.

10. The barbed suture of claim 6, wherein the weft stitched chain stitch is twisted.

11. The barbed suture of claim 6, wherein the weft stitched chain stitch is stretched.

12. The barbed suture of claim 1, wherein the first biocompatible material and the second biocompatible material are each selected from the group consisting in polyethylene, polypropylene, polyester such as polyethylene terephthalates, polyamide, silicone, polyether ether ketone (PEEK), polyarylether ether ketone (PAEK) polylactic acid (PLA), polycaprolactone (PCL), polydioxanone (PDO), trimethylene carbonate (TMC), polyvinyl alcohol (PVA), polyhydroxyalkanoate (PHA), polyglycolic acid (PGA), copolymers of these materials, and mixtures thereof.

13. A barbed suture comprising
    a knit elongate body including at least one weft stitched chain stitch, and
    at least one barb extending from the knit elongate body, the at least one barb including a monofilament cut formed from a weft stitch of the weft stitched chain stitch.

14. The barbed suture of claim 13, wherein the knit elongate body further comprises a plurality of chain stitches formed from chain stitch yarns.

15. The barbed suture of claim 14, wherein the chain stitch yarns are monofilament yarns.

16. The barbed suture of claim 14, wherein the chain stitch yarns are multifilament yarns.

17. The barbed suture of claim 16, wherein the multifilament chain stitch yarns have a tensile strength ranging from about 25 cN/dTex to about 40 cN/dTex.

18. The barbed suture of claim 14, wherein the chain stitch yarns are polyethylene multifilament yarns having a tensile strength of about 35 cN/dTex and the weft stitch is formed from weft yarns made of polypropylene monofilaments.

19. The barbed suture of claim 13, wherein the weft stitched chain stitch is heat-set.

20. The barbed suture of claim 13, wherein the weft stitched chain stitch is twisted.

21. The barbed suture of claim 13, wherein the weft stitched chain stitch is stretched.

22. The barbed suture of claim 13, wherein one or more of the elongate body or the at least one barb is made from a bioabsorbable material.

23. The barbed suture of claim 13, wherein an integrity of the elongate body is unaffected by the one or more barbs.

* * * * *